United States Patent
Sampson et al.

(10) Patent No.: US 10,689,680 B2
(45) Date of Patent: Jun. 23, 2020

(54) PAIRING CODE DIRECTED ASSEMBLY

(71) Applicant: Agilent Technologies, Inc., Santa Clara, CA (US)

(72) Inventors: Jeffrey Robert Sampson, San Jose, CA (US); Derek Lee Lindstrom, Cupertino, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 158 days.

(21) Appl. No.: 15/953,784

(22) Filed: Apr. 16, 2018

(65) Prior Publication Data

US 2018/0237818 A1 Aug. 23, 2018

Related U.S. Application Data

(63) Continuation of application No. 14/649,111, filed as application No. PCT/US2013/068549 on Nov. 5, 2013, now Pat. No. 9,976,162.

(60) Provisional application No. 61/735,345, filed on Dec. 10, 2012, provisional application No. 61/769,054, filed on Feb. 25, 2013.

(51) Int. Cl.
*C12P 19/34* (2006.01)
*C12N 15/10* (2006.01)
*C12N 15/64* (2006.01)
*C12N 15/66* (2006.01)

(52) U.S. Cl.
CPC .............. *C12P 19/34* (2013.01); *C12N 15/10* (2013.01); *C12N 15/64* (2013.01); *C12N 15/66* (2013.01)

(58) Field of Classification Search
CPC .............. C12N 15/66; C12Q 2521/313; C12Q 2525/131
See application file for complete search history.

(56) References Cited

U.S. PATENT DOCUMENTS

| | | | |
|---|---|---|---|
| 5,023,171 | A | 6/1991 | Ho et al. |
| 2004/0235035 | A1 | 11/2004 | Latrop et al. |
| 2007/0231805 | A1 | 10/2007 | Baynes |
| 2009/0155858 | A1 | 6/2009 | Blake |
| 2010/0136633 | A1 | 6/2010 | Serber et al. |

OTHER PUBLICATIONS

Czar, et al., "Gene synthesis demystified", Trends in Biotechnology, vol. 27, No. 2, 2009, pp. 63-72.
Jakobi, et al., "A Rapid Cloning Method Employing Orthogonal End Protection", PLoS One, 2012; 7(6): e37617, pp. 1-9.
Hughes, et al., "Gene synthesis: methods and applications", Methods Enzymol, 2011;498, pp. 277-309.

*Primary Examiner* — David C Thomas

(57) ABSTRACT

Methods for making a synthetic nucleic acid which comprise:
(a) identifying a conflicting nucleotide sequence in a target sequence;
(b) inserting a masking sequence into the conflicting sequence to produce a disrupted target sequence, wherein:
 (i) the masking sequence comprises recognition sites for one or more Type IIS restriction endonucleases; and
 (ii) digestion of said disrupted target sequence by said one or more Type IIS restriction endonucleases followed by re-ligation reconstitutes the target sequence;
(c) synthesizing a polynucleotide comprising the disrupted target sequence using polymerase chain assembly; and
(d) removing the masking sequence from said polynucleotide by digesting said polynucleotide with said one or more Type IIS restriction endonucleases followed by re-ligation of the digestion product, thereby producing a polynucleotide comprising said target sequence.

19 Claims, 6 Drawing Sheets

Specification includes a Sequence Listing.

1. A DNA template contains a BsaI restriction site (GGTCTC) that will interfere with assembly.
CGGCCGCACTTCAGATGGCGGTCTCTCTGACCCCAGAGCAGGT (SEQ ID NO: 1)

2. The site is disrupted *in silico* by inclusion of a removable intron
CGGCCGCACTTCAGATGGCGGTCTAGAGACGGATCTATACACGCCGGTGGTCGTCTCTCCGTCTCTCTGACCCCAGAGCAGGT (SEQ ID NO: 2)

3. After assembly, the nascent synthon is digested with an enzyme to leave single stranded overhangs
CGGCCGCACTTCAGATGGCGGTCTAGAGACGGATCTATACACGCCGGTGGTCGTCTCTCCGTCTCTCTGACCCCAGAGCAGGT (SEQ ID NO: 3)

4. Ligation of the single stranded overhangs generates the unaltered DNA template
CGGCCGCACTTCAGATGGCGGTCTCTCTGACCCCAGAGCAGGT (SEQ ID NO:4)

FIG. 6

SEQUENCE LISTING

<160> NUMBER OF SEQ ID NOS: 4

<210> SEQ ID NO 1
<211> LENGTH: 43
<212> TYPE: DNA
<213> ORGANISM: Artificial Sequence
<220> FEATURE:
<223> OTHER INFORMATION: Synthetic nucleic acid sequence

<400> SEQUENCE: 1
cggccgcact tcagatggcg gtctctctga ccccagagca ggt            43

<210> SEQ ID NO 2
<211> LENGTH: 83
<212> TYPE: DNA
<213> ORGANISM: Artificial Sequence
<220> FEATURE:
<223> OTHER INFORMATION: Synthetic nucleic acid sequence

<400> SEQUENCE: 2
cggccgcact tcagatggcg gtctagagac ggatctatac acgccggtgg tcgtctctcc      60
gtctctctga ccccagagca ggt                                              83

<210> SEQ ID NO 3
<211> LENGTH: 83
<212> TYPE: DNA
<213> ORGANISM: Artificial Sequence
<220> FEATURE:
<223> OTHER INFORMATION: Synthetic nucleic acid sequence

<400> SEQUENCE: 3
cggccgcact tcagatggcg gtctagagac ggatctatac acgccggtgg tcgtctctcc      60
gtctctctga ccccagagca ggt                                              83

<210> SEQ ID NO 4
<211> LENGTH: 43
<212> TYPE: DNA
<213> ORGANISM: Artificial Sequence

```
<220> FEATURE:
<223> OTHER INFORMATION: Synthetic nucleic acid sequence

<400> SEQUENCE: 4
cggccgcact tcagatggcg gtctctctga ccccagagca ggt                              43
```

PAIRING CODE DIRECTED ASSEMBLY

CROSS-REFERENCE TO RELATED APPLICATIONS

This application is a continuation of U.S. patent application Ser. No. 14/649,111, filed Jun. 2, 2015, which is a US national stage of PCT/US2013/068549, filed Nov. 5, 2013, which claims its priority from U.S. provisional patent application 61/735,345, filed Dec. 10, 2012 and U.S. provisional application 61/769,054, filed Feb. 25, 2013, the entire disclosures of which are incorporated herein by reference.

BACKGROUND

Gene synthesis has become an important tool in many fields of recombinant DNA technology including heterologous gene expression, vaccine development, gene therapy and molecular engineering. The synthesis of nucleic acid sequences de novo is often more economical than classical cloning and mutagenesis procedures. There is a constant need for new ways for assembling synthetic sequences in vitro.

SUMMARY

Provided herein is a method comprising: (a) producing a first complex by annealing: (i) a first nucleic acid comprising, in order, a first unique sequence, a first central sequence and a second unique sequence; and (ii) a second nucleic acid comprising, in order, the second unique sequence, a second central sequence and a third unique sequence; wherein the first, second and third unique sequences do not hybridize with each other; (b) subjecting the first complex to multiple rounds of primer extension to extend the first and second nucleic acids using each other as a template, thereby producing a first product molecule that contains, in order, the first unique sequence, the first central sequence, the second unique sequence, the second central sequence and the third unique sequence; and (c) circularizing the first product molecule by intramolecularly ligating the ends of the product molecule together. Kits and compositions relating to the method are also provided.

Also provided herein is a method for making a synthetic nucleic acid, comprising: (a) identifying a conflicting nucleotide sequence in a target sequence and (b) inserting a masking sequence into the conflicting sequence to produce a disrupted target sequence. In these embodiments, the masking sequence comprises recognition sites for one or more Type IIS restriction endonucleases and digestion of the disrupted target sequence by the one or more Type IIS restriction endonucleases followed by re-ligation reconstitutes the target sequence. This method further comprises (c) synthesizing a polynucleotide comprising the disrupted target sequence using polymerase chain assembly, and (d) removing the masking sequence from the polynucleotide by digesting the polynucleotide with the one or more Type IIS restriction endonucleases followed by re-ligation of the digestion product. A polynucleotide comprising the target sequence is produced.

The conflicting nucleotide sequence may be a recognition sequence for an enzyme. The enzyme may be a restriction enzyme. The conflicting sequences include those which interfere with hybridization during the polymerase chain assembly. Such conflicting sequences may be a repeat sequence, an AT-rich region of low sequence diversity, a GC-rich region of low sequence diversity, or a homopolymeric tract.

In some embodiments, the target sequence may be a protein coding sequence. In some embodiments, the target sequence encodes a regulatory RNA. The methods may further comprise enzymatically processing the polynucleotide between steps (c) and (d). The enzymatically processing may comprise circularizing the polynucleotide to produce a circular product. The enzymatically processing may further comprise removing sequences from the polynucleotide by digesting the circular product with one or more restriction enzymes, followed by re-ligation, wherein the restriction enzymes do not digest the masking sequences.

The present methods for making a synthetic nucleic acid may be performed on a polynucleotide in linear form. Type IIS restriction enzymes include BsaI, BsmB1, BbsI, SfaNI and HgaI.

In some embodiments, the masking sequence may comprise two sites for a single Type IIS restriction enzyme. In some embodiments, the masking sequence is of 12-50 nucleotides in length.

In some embodiments, the present method may further comprise (e) cloning the target sequence into a vector. Suitable vectors include an expression vector designed for expression of the target sequence. This embodiment may further comprise transferring the expression vector into a cell to produce an expression product encoded by the target sequence. The expression product may be tested for an activity. The method may be performed with the masking sequence which is in the overlapping region between two overlapping oligonucleotides used in the polymerase chain assembly.

BRIEF DESCRIPTION OF THE FIGURES

The skilled artisan will understand that the drawings, described below, are for illustration purposes only. The drawings are not intended to limit the scope of the present teachings in any way.

FIG. 6 illustrates a method in which a BsaI site is masked during assembly.

DEFINITIONS

Figure 1:
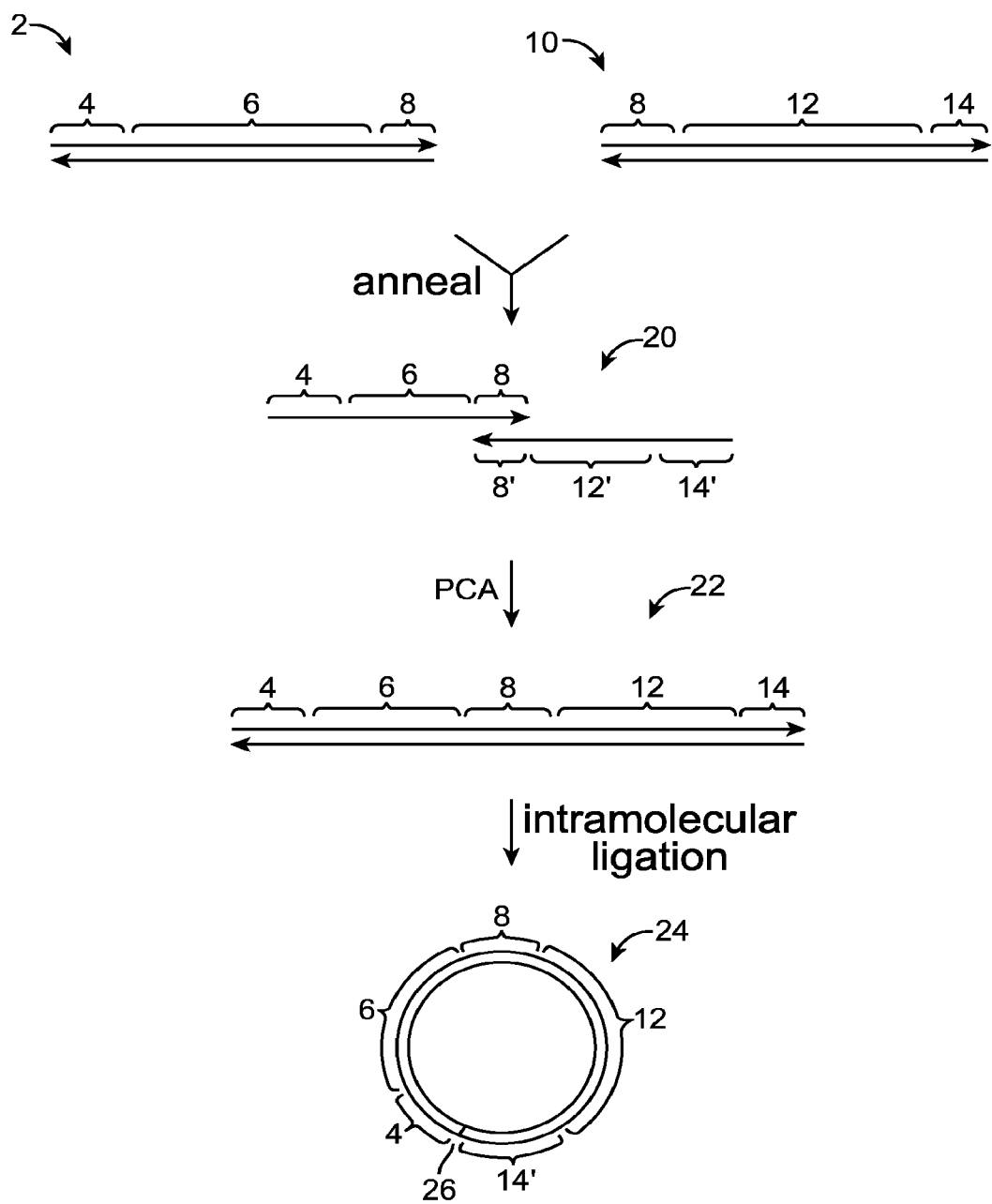
FIG. 1 schematically illustrates one embodiment of the subject method.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence of the strand to hybridize therewith and thereby form the template for the synthesis of the extension product.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "Selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42 C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times (e.g., at least 5 or 10 times, up to 30 or 40 or more times) such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

As used herein, the term "Tm" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+])+0.41$ (fraction G+C)−(60/N), where N is the chain length and $[Na^+]$ is less than 1 M. See Sambrook and Russell (2001; Molecular Cloning: A Laboratory Manual, $3^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

The term "free in solution," as used here, describes a molecule, such as a polynucleotide, that is not bound or tethered to another molecule.

The term "ligating", as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

The term "digesting" is intended to indicate a process by which a nucleic acid is cleaved by a restriction enzyme. In order to digest a nucleic acid, a restriction enzyme and a nucleic acid containing a recognition site for the restriction enzyme are contacted under conditions suitable for the restriction enzyme to work. Conditions suitable for activity of commercially available restriction enzymes are known, and supplied with those enzymes upon purchase.

A "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the Tm of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired.) Nucleic acid may also be denatured chemically (e.g., using urea or NaOH).

The term "extending", as used herein, refers to the extension of a primer by the addition of nucleotides using a polymerase. If a primer that is annealed to a nucleic acid is extended, the nucleic acid acts as a template for extension reaction.

The term, "intramolecularly ligating" refers to a ligation in which the 5' end and the 3' end of a strand of nucleic acid are ligated to one another to produce a circular DNA molecule.

The term "re-circularizing", as used herein, refers to the intramolecular ligation of a linearlized molecule that was previously circular.

The term "unique sequence", as used herein, refers to nucleotide sequences that are different one another, or their complements. For example, a first unique sequence has a different nucleotide sequence than a second unique sequence or its complement. Unless otherwise indicated, a unique sequence is only present in one polynucleotide in a sample.

The term "do not hybridize to each other", as used herein in the context of nucleic acids that do not hybridize to each other, refers to sequences that been designed so that they do not anneal to one another under stringent conditions. Such sequences, called "sequence tokens" in certain publications, are described in, e.g., US20070259357 and Brenner et al (Proc. Natl. Acad. Sci. 1992 89:5381-3), which are incorporated by reference herein.

The term "synthon", as used herein, refers to a synthetic nucleic acid that has been assembled in vitro from several shorter nucleic acids.

The term "immediately adjacent", as used herein, means operably linked. For example, two coding sequences are immediately adjacent to one another if they can be transcribed and translated into a protein in a cell. In certain cases, the term "immediately adjacent" means that there are no intervening nucleotides between two sequences.

The term "similar to one another" in the context of a polynucleotide or polypeptide, means sequences that are at least 70% identical, at least 80% identical, at least 90% identical, or at least 95% identical, to one another.

The term "conflicting nucleotide sequence", as used herein, refers to a sequence that, if present, would interfere with one or more steps in a pre-defined protocol. For example, some protocols may require adding a site for a restriction enzyme to a target sequence, and then digesting the target sequence using the restriction enzyme. In this example, if the target sequence already contains the restriction site, then that site would be a conflicting nucleotide sequence. In another case, a conflicting sequence may interfere with hybridization in a polymerase chain assembly reaction. In this case, the sequence may be a repeated sequence, an AT-rich region of low sequence diversity, a GC-rich region of low sequence diversity, or a homopolymeric tract, for example.

The term "masking sequence", as used herein, refers to a sequence that can be inserted into a conflicting nucleotide sequence in order to change its sequence and thereby prevent it from interfering with a step that occurs later in the protocol.

The term "disrupted target sequence", as used herein, refers to a target sequence (i.e., a sequence that one wishes to synthesize) into which a masking sequence has been inserted.

The phrase "digestion . . . followed by re-ligation", as used herein, refers to a protocol in which a disrupted nucleic acid is first digested with a restriction enzyme to release a fragment, and the resultant nucleic acid (minus the fragment) is re-ligated together to provide a product that is essentially the same as the disrupted nucleic acid, but without the fragment.

The term "reconstitutes the target sequence", as used herein, refers to re-making a polynucleotide that has the original target sequence.

The term "polymerase chain assembly", as used herein, refers to a protocol in which multiple overlapping oligonucleotides are combined and subjected to multiple rounds of primer extension (i.e., multiple successive cycles of primer extension, denaturation and renaturation in the presence of a polymerase and nucleotides) to extend the oligonucleotides using each other as a template, thereby producing a product molecule. In many cases, the final product molecule is amplified using primers that bind to sites at the ends of the product molecule, and the product molecule is digested with one or more restriction enzymes and cloned. Polymerase chain assembly may include additional steps, such as digestion of the product molecule with a restriction enzyme to, e.g., prepare the product molecule for cloning. In other cases and as will be described in greater detail below, the product molecule may be digested to remove one or more sequences from the product molecule, e.g., using the Type IIS restriction enzyme-based methods described below.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

With reference to FIG. 1, one embodiment of the method comprises: producing a first complex 20 by annealing: (i) a first nucleic acid 2 comprising, in order, a first unique sequence 4, a first central sequence 6 and a second unique sequence 8; and (ii) a second nucleic acid 10 comprising, in order, the second unique sequence 8, a second central sequence 12 and a third unique sequence 14. As shown in FIG. 1, the first, second and third unique sequences do not hybridize with each other and, because the same sequence (i.e., unique sequence 8) is present at the 3' end of the first nucleic acid and the 5' end of the second nucleic acid, the top strand of the first nucleic acid and the bottom strand of the second nucleic acid hybridize in this region to provide the first complex. As shown, the first complex comprises at least the top strand of the first nucleic acid and the bottom strand of the second nucleic acid (comprising the complement of the second unique sequence 8', the complement of the second central sequence 12' and the complement of the third unique sequence 14', hybridized by the second sequence 8 and its complement 8'. As shown, the initial first and second nucleic acids (2 and 10) are double stranded molecules. In other embodiments, complex 20 can be made using molecules that are single stranded.

After complex 20 is produced, the method may comprise subjecting the first complex 20 to multiple rounds of primer extension (i.e., multiple successive cycles of primer extension, denaturation and renaturation in the presence of a polymerase and nucleotides) to extend the first and second nucleic acids using each other as a template, thereby producing a first product molecule 22 that contains, in order, the first unique sequence 4, the first central sequence 6, the second unique sequence 8, the second central sequence 12 and the third unique sequence 14. After the first product molecule 22 is produced, the method may comprise circularizing the first product molecule by intramolecularly ligating the ends of the product molecule together. As shown, circularized product molecule 24 comprise first unique sequence 4, the first central sequence 6, the second unique sequence 8, the second central sequence 12 and the third unique sequence 14. As indicated, circularized product molecule 24 contains a ligation site 26 between first unique sequence 4 and third unique sequence 14. In particular embodiments, the first unique sequence 4 and the unique sequence at the other end of the first product molecule 22 may comprise a restriction site, and the first product molecule 22 may be cut at those sites prior to intramolecular ligation to provide compatible ends. In alternative embodiments, the ends of the product molecule 22 may be polished by treatment with another enzyme. Suitable conditions for performing multiple rounds of primer extension to obtain a linear product may be adapted from the polymerase chain assembly methods found in, e.g., Hughes, et al. (Methods in Enzymology 2011 498:277-309) and Wu, et al. (J. Biotechnol. (2006), 124:496-503).

As will be described in greater detail below, in certain embodiments, further initial nucleic acids may be used (e.g., a third, fourth, fifth and/or sixth or more nucleic acids), can be joined together and circularized using this method. In these embodiments, the further initial nucleic acids contain overlapping unique sequences at their ends that allow them to hybridize with one another and be extended in the same way as shown in FIG. 1.

After the circularized product molecule 24 has been made, the unique sequence may be removed from the circularized product molecule using one or more Type IIS restriction enzymes, which cleave DNA at a defined distance from their recognition sites. Type IIS restriction enzymes include, but are not limited to: AlwI, BccI, BsmAI, EarI, MlyI, PleI, BmrI, BsaI, BsmBI, FauI, HpyAV, MnlI, SapI, BbsI, BciVI, HphI, MboII, BfuaI, BspMI, SfaNI, HgaI, BbvI, EciI, FokI, BceAI, BsmFI, BtgZI, BpmI, BpuEI, BsgI, Ac1WI, A1w26I, Bst6I, BstMAI, Eam1104I, Ksp632I, PpsI, SchI, BfiI, Bso31I, BspTNI, Eco31I, Esp3I, FauI, SmuI, BfuI, BpiI, BpuAI, BstV2I, AsuHPI, Acc36I, LweI, AarI, BseMII, TspDTI, TspGWI, BseXI, BstV1I, Eco57I, Eco57MI, GsuI, PsrI, and MmeI.

Figure 2A:
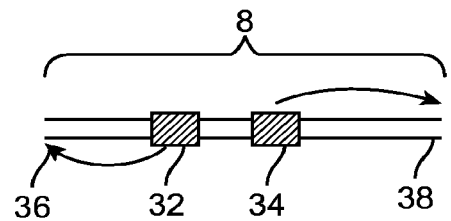
FIGS. 2A and 2B illustrate a second embodiment of the subject method.

A possible strategy for this step is schematically illustrated in FIG. 2A, which shows second unique sequence 8 that contains two Type IIS restriction enzyme recognition sites 32 and 34, which cleave on either side of the second unique sequence at sites 36 and 38, respectively. In certain embodiments, the recognition sites 32 and 34 may be the same sequence on different strands (in which case the same enzyme can cleave at both sites 36 and 38). Alternatively, recognition sites 32 and 34 may be different sequences, which case two different enzymes may be used to cleave at sites 36 and 38). The sequences used should be designed so that cleavage at sites 36 and 38 by the one or more Type IIS restriction enzymes results in ends that can be ligated to one another (e.g., that contain compatible overhangs). In this embodiment of the method and as shown in FIG. 2A, the second unique sequence 8 may comprises recognition sites 32 and 34 for one or more Type IIS restriction endonucleases, wherein the cleavage sites for the one or more Type IIS restriction endonucleases 36 and 38 are on either side of the second unique sequence.

Figure 2B:
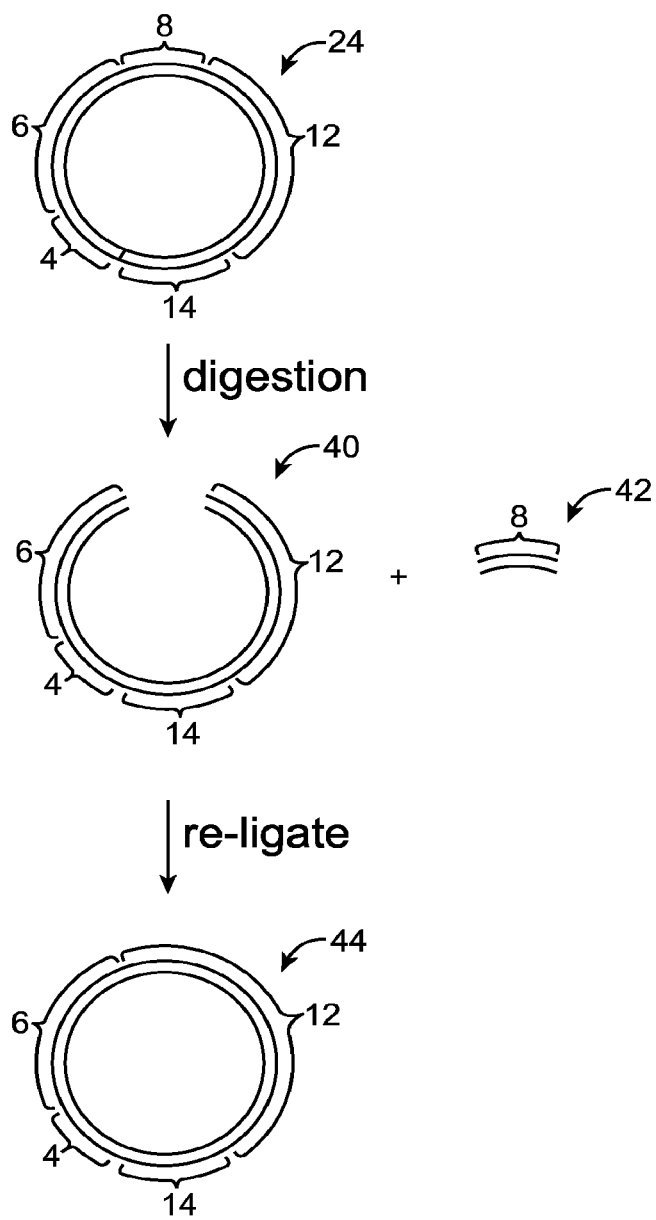

In this embodiment and with reference to FIG. 2B, the method may further comprise digesting the circularized product molecule 24 with the one or more Type IIS restriction enzymes, thereby producing a linear product molecule 40 that does not contain the second unique sequence and, as a separate molecule 42, the second unique sequence 8. The method then involves re-circularizing the linear product molecule 40 by intramolecularly ligating the ends of the linear product molecule together, thereby producing a second circular product molecule 44 that contains a synthon in which the first central sequence 6 and the second central sequence 12 are immediately adjacent to each other. This intramolecular ligation step may be facilitated by diluting the reaction so that intramolecular ligation is favored.

As would be recognized, this method for removing a unique sequence (which involves cutting with one or more Type IIS restriction enzymes to excise a unique sequence, and then intramolecularly religating the ends of the product molecule) can be repeated sequentially using different Type IIS restriction enzymes to remove other unique sequences if they are present in the circularized product molecule 24. In certain cases, the sample that contains circularized product molecule 24 may be treated with an exonuclease to remove any uncircularized product molecules prior to digestion.

In certain embodiments, the method may further comprise cloning the synthon out of product molecule 44 into a vector. This may be done in a variety of different ways. In one embodiment, at least the first unique sequence 4 (e.g., the first unique sequence and unique sequence at the other end of the synthon, for example, the third unique sequence) may comprise a restriction site, and the cloning is done by: digesting the re-circularlized product molecule 44 using a restriction enzyme that cleaves at the restriction site to produce a clonable fragment; and (g) ligating the synthon into a plasmid vector.

In other embodiments, the cloning may be done by amplifying the synthon of the re-circularlized product molecule 44 by PCR using PCR primers that bind to one or more sites in a least in the first unique sequence 4 (e.g., in the first unique sequence 4 and in the unique sequence at the other end of the synthon, for example, the third unique sequence); and cloning the amplified synthon into a plasmid vector. As would be understood, the PCR product may itself be digested by a restriction enzyme to facilitate cloning.

In particular cases, the first and second nucleic acid molecules may be designed so that the second unique sequence disrupts a conflicting sequence in the first product molecule (e.g., a site for a Type IIs restriction enzyme that is used later in the protocol or a sequence that might interfere with hybridization). For example, if the synthon contains a site for a restriction enzyme that is used in the process described herein, then that sequence can be masked by inserting a masking sequence into it. The masking sequence can then be removed using Type IIs restriction enzymes as described below.

The synthon itself can be of any sequence and, in certain cases, may encode a sequence of amino acids, i.e., may be a coding sequence. In other embodiments, the synthon can be a regulatory sequence such as a promoter or enhancer. In particular cases, the synthon may encode a regulatory RNA. In certain cases a synthon may have a biological or structural function.

In particular cases, vector may be an expression vector designed for expression of the synthon. In these embodiments, the expression vector may contain a promoter, terminator and other necessary regulatory elements to effect transcription and in certain cases translation of the synthon, either as a single protein, or as a fusion with another protein. In these embodiments, the method may further comprises transferring the expression vector into a cell to produce the expression product (e.g., a protein) encoded by the synthon. This embodiment of the method may comprise screening the expression product for an activity.

In certain cases, the first, second and third unique sequences (and any other non-hybridizing unique sequences that are used in the method) may be selected from a larger set of Tm-matched sequences (e.g., a set of at least 10, at least 20, up to 50 or 100 sequences) that do not cross-hybridize with one another, where the term "$T_m$-matched" refers to a set of oligonucleotides that have $T_m$s that are within a defined range, e.g., within 5° C. or 10° C. of one another. Sets of non-cross-hybridizing sequences are described in, e.g., US20070259357, US20030077607, US20100311957, and Brenner et al (Proc. Natl. Acad. Sci. 1992 89:5381-3). Further, computer algorithms for selecting non-crosshybridizing sets of sequences are described in Brenner (PCT Publications No. WO 96/12014 and WO 96/41011) and Shoemaker (Shoemaker et al., European Pub. No. EP 799897 A1 (1997)). Typically, a segment of unique sequence is from 10 to 60 bases in length, e.g., 10 to 30 bases in length. In some embodiments, a unique sequence may contain one or more sites for one or more Type IIS restriction enzyme, as described above.

As noted above, in certain embodiments, three, four, five or six or more initial nucleic acid can be joined together and circularized using this method.

For example the first complex may further comprise a third nucleic acid comprising, in order, the third unique sequence, a third central region and a fourth unique sequence, wherein the first, second, third and fourth unique sequences do not hybridize with each other and the product molecule of step (b) comprises, in order, the first unique sequence, the first central region, the second unique sequence, the second central sequence, the third unique sequence, the third central sequence and the forth unique sequence.

In other example, the first complex may further comprise: a third nucleic acid comprising, in order, the third unique sequence, a third central region and a fourth unique sequence; a fourth nucleic acid comprising, in order, the fourth unique sequence, a fourth central region and a fifth unique sequence. In this example, the first, second, third, fourth and fifth unique sequences do not hybridize with each other; and the product molecule may comprise, in order, the first unique sequence, the first central region, the second unique sequence, the second central sequence, the third unique sequence, the third central sequence region, the forth unique sequence, the fourth central region and the fifth unique sequence.

The unique sequences can be excised from the circular product molecules if the different unique sequences contain recognition sites for different Type IIS restriction endonuclease. In these embodiments, one unique sequence can be excised by digestion with a Type IIS restriction endonuclease using the strategy outlined above, and the linear product re-circularized. The re-circularized product can then be digested by a second Type IIS restriction endonuclease to remove another unique sequence, and then re-circularized. For example, in one embodiment, the second unique sequence may comprise recognition sites for a first Type IIS restriction endonuclease and the third unique sequence comprises recognition sites for a second Type IIS restriction endonuclease, and the cleavage sites for the first and second Type IIS restriction endonucleases are on both sides of the second and third unique sequences, respectively. These embodiments may comprise removing the second and third unique sequences by: i. digesting the circularized product molecule with the first Type IIS restriction enzyme to produce a first linear product molecule that does not contain the second unique sequence; and ii. re-circularizing the first linear product molecule by intramolecularly ligating the ends of the linear product molecule together; iii. digesting the re-circularized product molecule of ii. with the second Type IIS restriction enzyme to produce a second linear product molecule that does not contain the third unique sequence; and iv. re-circularizing the second linear product molecule by intramolecularly ligating the ends of the second linear product molecule together. This method produces a synthon in which the first central sequence, the second central sequence and the third central sequence are immediately adjacent to each other. Further unique sequences can be removed using a similar strategy.

The above-described method can be used in a variety of gene synthesis applications. For example, the method can be employed to make two or more different synthons in the same reaction vessel. In these embodiments, the method may comprise (a) producing, in the same reaction vessel as the first complex, a second complex by annealing: (i) a third nucleic acid comprising, in order, a fourth unique sequence, a third central sequence and a fifth unique sequence; and (ii) a fourth nucleic acid comprising, in order, the fifth unique sequence, a fourth central sequence and a sixth unique sequence; wherein the first, second, third, fourth, fifth and sixth unique sequences do not hybridize with each other. This embodiment of the method may comprise (b) subjecting the first and second complexes to multiple rounds of primer extension to extend the first, second, third and fourth nucleic acids, thereby producing, in addition to the first product molecule, a second product molecule that contains, in order, the fourth unique sequence, the third central sequence, the fifth unique sequence, the fourth central sequence, and the sixth unique sequence. This embodiment may comprise (c) circularizing, in the same reaction vessel, the first and second product molecules by independently intramolecularly ligating the ends of the first and second product molecules together.

After the first and second product molecules are produced, the method may comprise removing the unique sequences from the middle of each of the product molecules to produce two different synthons. In this embodiment, the second unique sequence may comprise recognition sites for a Type IIS restriction endonuclease and the fifth unique sequence may comprises recognition sites for the same Type IIS restriction endonuclease, where the cleavage sites for the Type IIS restriction endonucleases are on both sides of the second and fifth unique sequences, respectively. In this embodiment, the second and fifth sequences may be removed by digesting, in the same reaction vessel, the circularized product molecules with the Type IIS restriction enzyme, thereby producing linear product molecules that do not contain the second or fifth unique sequence; and re-circularizing the linear product molecules by intramolecularly ligating the ends of the linear product molecules together. This step of the method should result in i. a first synthon in which the first and second central sequences are immediately adjacent to each other; and ii. a second synthon in which the third and fourth central sequences are immediately adjacent to each other.

Certain embodiments may be used to assemble multiple synthons in the same reaction vessel. For example, certain embodiments may be used assemble at least 2, at least 5, at least 10, at least 50, at least 100, at least 500, at least 1,000 or more synthons in the same reaction vessel. The embodiment described may be particularly useful for assembling, in the same reaction vessel, several variants of the same sequence, where the sequences of the variants are similar to one another. In certain cases, the nucleotide sequences of one or more of the central sequences (e.g., the first and second central sequences in the example shown above) may be similar to one another. For example, in certain cases, two or more central sequences within a single synthon may be similar to one another. In other embodiments, the nucleotide sequences of different synthons may be similar to one another.

In other embodiments, the method may also be used to generate different combinations of central sequences. For example, in one embodiment, the method may be used to make, for example several synthons that each contain a first central sequence and vary in that they contain different second central sequences.

The length of the central sequences, the unique sequences and the synthon may vary greatly. In certain embodiments, a central sequence may be of 20 to 500 bp in length, whereas the unique sequences may be of 10 to 50 bp in length. The length of the synthon product may be from, for example, 200 bp to 10 kb or more in length.

Figure 3:
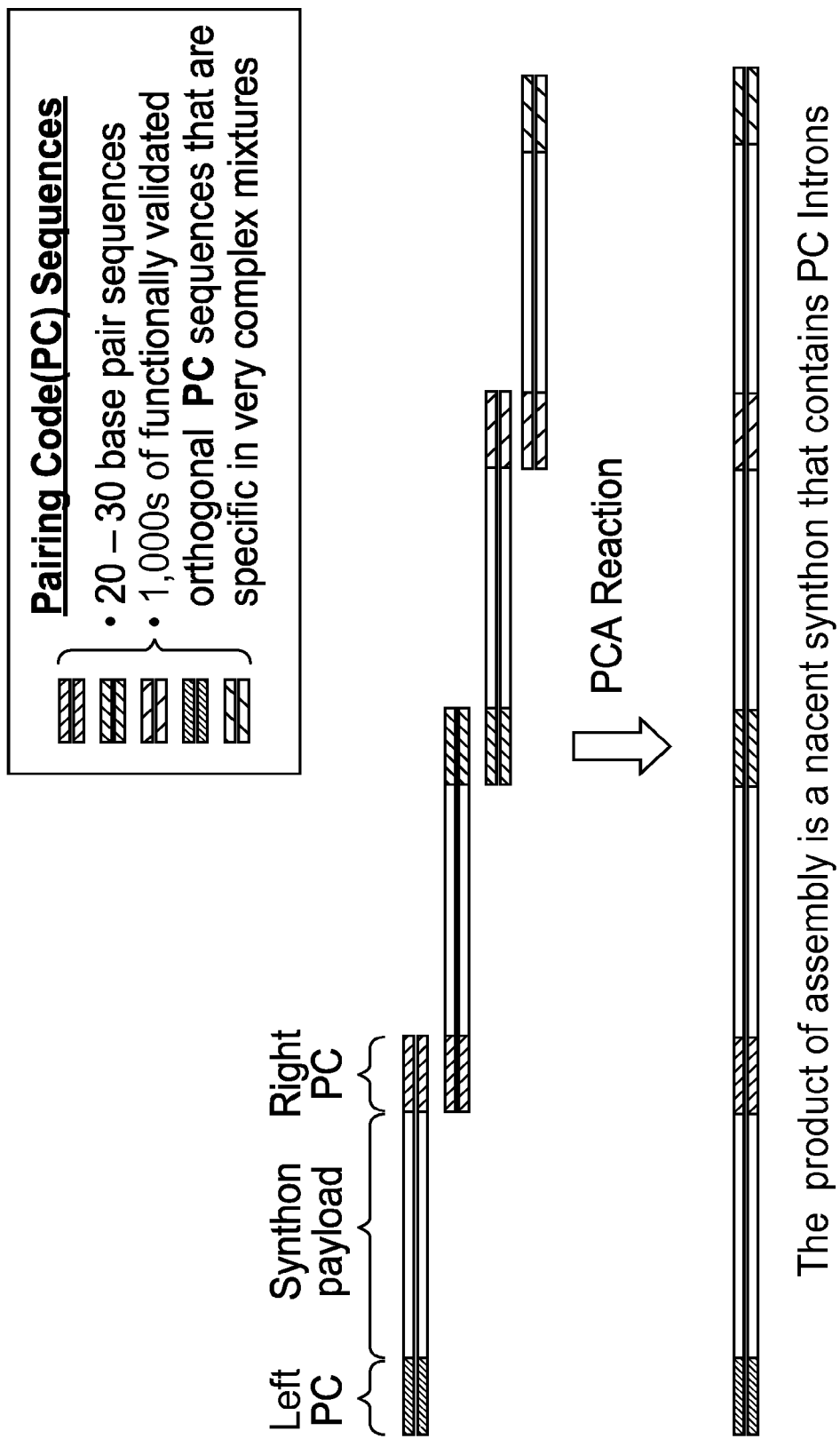
FIG. 3 illustrates an exemplary embodiment of the method.
Figure 4:
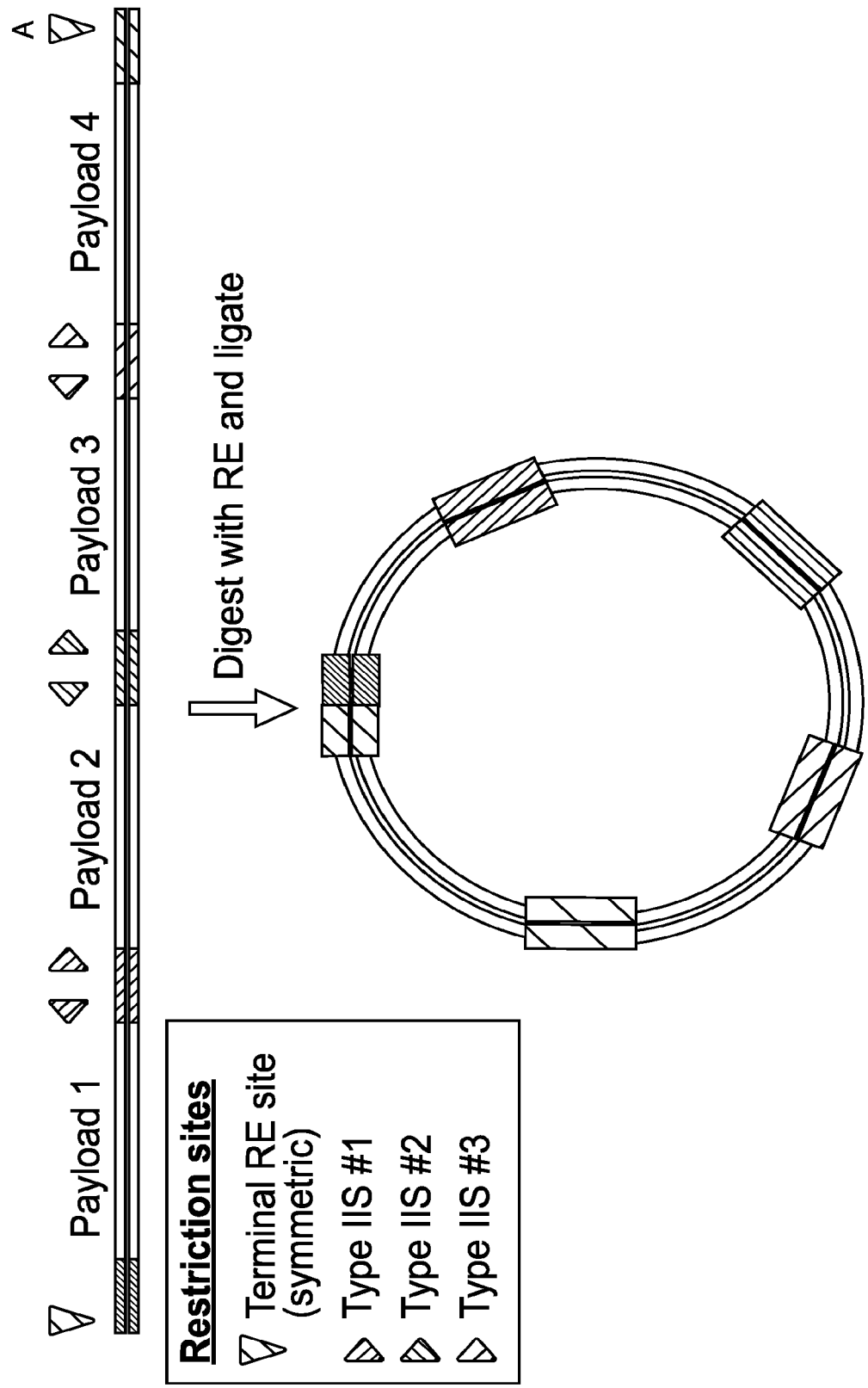
FIG. 4 illustrates a further embodiment of the method.

The initial steps of one embodiment of the method are illustrated in FIG. 3. In this embodiment, four initial nucleic acid fragments contain appropriate orthogonal pairing code "PC" sequences are assembled into one linear product using polymerase chain assembly "PCA" using the pairing codes to direct the assembly. Next, with reference to FIG. 4, the linear product is digested at a restriction site that is present in the terminal pairing code sequences, and the digested product is circularized via an intramolecular ligation. Next, the assembled product undergoes maturation in which the pairing code sequences are removed. In this embodiment, each of the pairing code sequences include a unique restriction site in its termini to allow ends to be cut and ligated together to form a circular nascent synthon. In this embodiment, each pairing code sequence is flanked by Type IIS restriction sites that cut within the flanking payload sequence to leave sticky ends. Sequentially digestion and ligation of the nascent synthon under conditions that favor intramolecular ligation removes the pairing code sequences.

Also provided by this disclosure an aqueous composition comprising a mixture of: (i) a first nucleic acid comprising, in order, a first unique sequence, a first central sequence and a second unique sequence; and (ii) a second nucleic acid comprising, in order, the second unique sequence, a second central sequence and a third unique sequence; wherein the first, second and third unique sequences do not hybridize with each other. Other components of the composition may be described in the context of the method discussed above.

Figure 5:
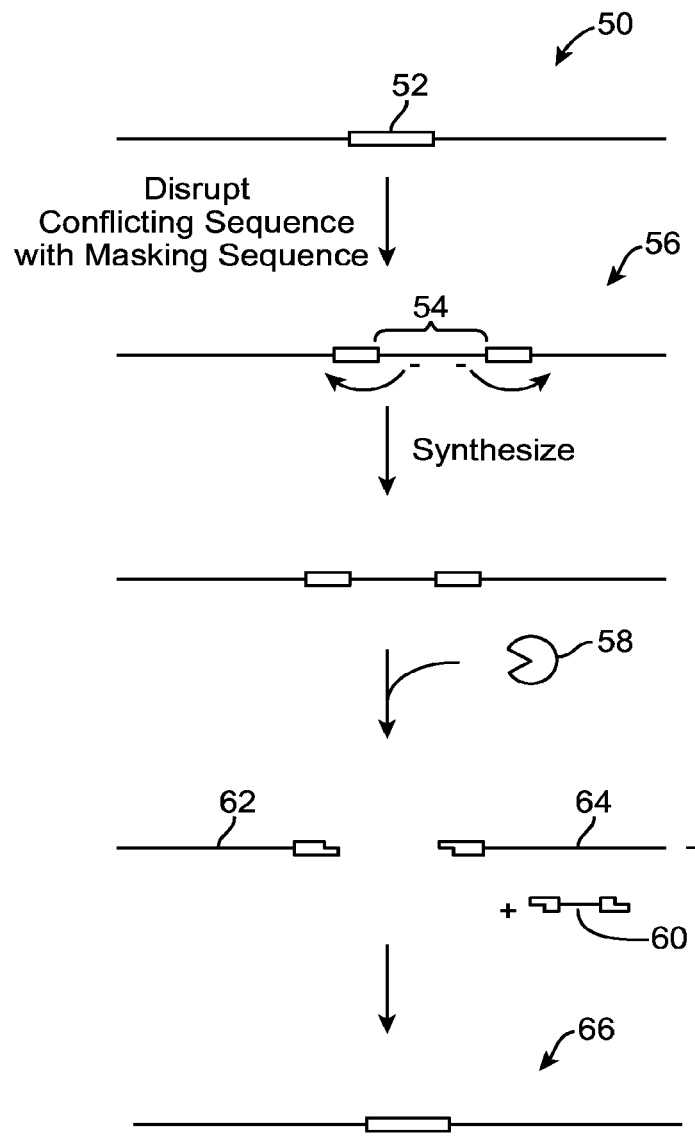
FIG. 5 illustrates an embodiment in which a conflicting sequence is masked by a masking sequence.

A related embodiment provides a method for making a synthetic nucleic acid. With reference to FIG. 5, this method comprises analyzing the sequence of target sequence 50 (i.e., a sequence that is to be made synthetically using polymerase chain assembly) to identify conflicting nucleotide sequence 52, where the conflicting sequence, if it is left in the target sequence, would interfere with downstream step in the protocol. Exemplary conflicting sequences include, but are not limited to, a recognition sequence for an enzyme, e.g., a restriction enzyme such as a Type IIS restriction enzyme, a binding site for a primer or a bacteriophage promoter, or a sequence that is predicted to interfere with hybridization during polymerase chain assembly, e.g., a repeat sequence, an AT-rich region of low sequence diversity, a GC-rich region of low sequence diversity, or a homopolymeric tract, for example. After the conflicting sequence has been identified, masking sequence 54 is inserted into conflicting sequence 52 to produce a disrupted target sequence 56. As indicated, the masking sequence is designed so that it comprises recognition sites for one or more Type IIS restriction endonucleases, and digestion of the disrupted target sequence by the one or more Type IIS restriction endonucleases followed by re-ligation reconstitutes the target sequence. The masking sequence can be of any length. However, in many cases, the masking sequence may be 12-50 nucleotides in length.

Once disrupted target sequence 56 has been designed, the method comprises synthesizing polynucleotide 58 (which comprises the disrupted target sequence) using polymerase chain assembly. As noted above, polymerase chain assembly involves subjecting multiple overlapping oligonucleotides to multiple rounds of primer extension (i.e., multiple successive cycles of primer extension, denaturation and renaturation in the presence of a polymerase and nucleotides) to extend the oligonucleotides using each other as a template, thereby producing a product molecule, and then amplifying the final product molecule using primers that bind to sites at the ends of the product molecule. Exemplary conditions for performing polymerase chain assembly methods are found in, e.g., Hughes, et al. (Methods in Enzymology 2011 498:277-309) and Wu, et al. (J. Biotechnol. (2006), 124: 496-503), which are incorporated by reference. After polymerase chain assembly, the masking sequence can be removed from the polynucleotide 56 by digesting polynucleotide 56 with the one or more Type IIS restriction endonucleases 58 to release the masking sequence 60, followed by re-ligation of the digestion products 62 and 64, thereby producing a polynucleotide 66 that comprises the reconstituted target sequence 50. In these embodiments, the released masking sequence 60 may be removed from the reaction by chromatography (e.g., size exclusion chromatography), or any other method for removing small fragments from a reaction, if desired.

In certain embodiments, this method may further comprise enzymatically processing the polynucleotide after being synthesized and before the masking sequence is removed. For example, in one embodiment, the ends of the polynucleotide may be ligated together intramolecularly to produce a circular product. In other embodiments and as shown in FIG. 5, the masking sequences may be removed from a molecule in linear form. The overhangs generated by cleavage by the Type IIS restriction endonuclease should be compatible with one another and should ligate to one another efficiently even if the disrupted sequence is linear. In embodiments in which the disrupted sequence has been circularized, the circularized product may be enzymatically processed by removing sequences from the polynucleotide by digesting the circular product with one or more restriction enzymes, followed by re-ligation. In these embodiments, the restriction enzymes do not necessarily digest the masking sequence.

For example, in some embodiments, the target sequence may be made by designing a synthon and identifying a conflicting sequence (e.g., sites for one of more Type IIS restriction enzymes), inserting a masking sequence into the site, and making a disrupted target sequence by: (a) producing a first complex by annealing: (i) a first nucleic acid comprising, in order, a first unique sequence, a first central sequence and a second unique sequence; and (ii) a second nucleic acid comprising, in order, the second unique sequence, a second central sequence and a third unique sequence; wherein the first, second and third unique sequences do not hybridize with each other and wherein the second unique sequence comprises recognition sites for one or more Type IIS restriction endonucleases, wherein the cleavage sites for the one or more Type IIS restriction endonucleases are on either side of the second unique sequence; (b) subjecting the first complex to multiple rounds of primer extension to extend the first and second nucleic acids using each other as a template, thereby producing a first product molecule that contains, in order, the first unique sequence, the first central sequence, the second unique sequence, the second central sequence and the third unique sequence; (c) circularizing the first product molecule by intramolecularly ligating the ends of the product molecule together, (d) digesting the circularized product molecule of (c) with the one or more Type IIS restriction enzymes, thereby producing a linear product molecule that does not contain the second unique sequence; and (e) re-circularizing the linear product molecule by intramolecularly ligating the ends of the linear product molecule together, thereby producing a synthon in which the first central sequence and the second central sequence are immediately adjacent to each other and that contains the synthon. The masking sequence can then be removed from the disrupted synthon by digestion with another Type IIS restriction enzyme followed by re-ligation, as described above. In any of these embodiments, the one or more Type IIS restriction enzymes may be independently selected from AlwI, BccI, BsmA1, EarI, MlyI, PleI, BmrI, BsaI, BsmB1, FauI, HpyAV, MnlI, SapI, BbsI, BciVI, HphI, MboII, BfuaI, BspMI, SfaNI, HgaI, BbvI, EciI, FokI, BceAI, BsmFI, BtgZI, BpmI, BpuEI, BsgI, Ac1WI, Alw26I, Bst6I, BstMAI, Eam1104I, Ksp632I, PpsI, SchI, BfiI, Bso31I, BspTNI, Eco31I, Esp3I, FauI, SmuI, BfuI, BpiI, BpuAI, BstV2I, AsuHPI, Acc36I, LweI, AarI, BseMII, TspDTI, TspGWI, BseXI, BstV1I, Eco57I, Eco57MI, GsuI, PsrI, and MmeI, for example.

In certain cases, the masking sequence may contain sites for a single Type IIS restriction enzyme (where the same enzyme cuts at the both junctions of the masking sequence and the target sequence). In other cases, the masking sequence may contain sites for different Type IIS restriction enzymes (where one enzyme cuts at one junction between the masking sequence and the target sequence, and the other enzyme cuts at the other between the masking sequence and the target sequence). The ends generated by cleavage should be compatible (i.e., ligatable) to one another.

Similar to the methods described above, the target sequence may be a protein coding sequence or a regulatory RNA, for example. In particular embodiments, the method may further comprise cloning the target sequence into a vector. In some cases, vector may be an expression vector designed for expression of the target sequence. In these embodiments, the expression vector may contain a promoter, terminator and other necessary regulatory elements to effect transcription and in certain cases translation of the target sequence, either as a single protein, or as a fusion with another protein. In these embodiments, the method may further comprises transferring the expression vector into a cell to produce the expression product (e.g., a protein) encoded by the target sequence. This embodiment of the method may comprise screening the expression product for an activity.

In particular cases and consistent with the description set forth above, the masking sequence may be designed so that it is in the overlap between two of the overlapping oligonucleotide used in polymerase chain assembly. In this way, the masking sequence can direct the assembly of a synthon, as well as mask interfering sequences in the synthon. In some embodiments, the masking sequence may be a sequence selected from a set of non-cross-hybridizing sequences, as described in, e.g., US20070259357, US20030077607, US20100311957, and Brenner et al (Proc. Natl. Acad. Sci. 1992 89:5381-3). Computer algorithms for selecting non-crosshybridizing sets of sequences are described in Brenner (PCT Publications No. WO 96/12014 and WO 96/41011) and Shoemaker (Shoemaker et al., European Pub. No. EP 799897 A1 (1997)).

In one exemplary embodiment, the target sequence may comprise a site for a restriction enzyme that is to be used for cloning of the target sequence into a vector after it is made. This method can be used to mask the restriction site until after the target sequenced is cloned. In another embodiment, the target sequence may comprise a site for a Type IIS restriction enzyme that is used to remove a sequence from the target sequence after it is made. This method can be used to mask the Type IIS restriction site until after the sequence has been removed. Other types of sequences can be masked in this protocol.

Kits

Also provided by this disclosure is a kit for practicing the subject method, as described above. A subject kit may contain at least: (i) a first nucleic acid comprising, in order, a first unique sequence, a first central sequence and a second unique sequence; and (ii) a second nucleic acid comprising, in order, the second unique sequence, a second central sequence and a third unique sequence; wherein the first, second and third unique sequences do not hybridize with each other. The kit may also contain reagents for performing polymerase chain assembly (e.g., polymerase, nucleotides and buffer, etc.), and other enzymes and/or reagents for performing the method, e.g., one or more Type IIS restriction enzymes and ligases, etc. The various components of the kit may be present in separate containers or certain compatible components may be pre-combined into a single container, as desired.

In addition to above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The example shown below illustrates a method in which a BsaI site is masked during assembly.

Gene assembly by polymerase chain assembly begins with a design process that breaks a long sequence into shorter fragments consistent with the chosen assembly method. Undesirable DNA sequence elements can be identified during the design process and disrupted in silico by the inclusion of a DNA sequence encoding a removable "intron". The removable intron includes two type IIS restriction enzyme recognition sequences that direct staggered, double-stranded cleavage of the DNA sequences immediately adjacent to the intron. After gene assembly, digestion of the gene with the appropriate type IIS restriction enzyme will leave 4 base pair single-stranded DNA overhangs that can be ligated together to reconstitute the original DNA sequence element. Because the recognition sites of the type IIS enzyme are located within the intron, their elimination is irreversible after ligation. Because enzyme binding to restriction recognition sequences can be sterically hindered by nearby protein-DNA interactions, the type IIS sites may be physically separated by a 20 base pair long orthogonal DNA sequence (a non-cross-hybridizing sequence) to allow efficient removal. This example is illustrated in FIG. 6.

The invention claimed is:

1. A method for making a synthetic nucleic acid, comprising:
   (a) identifying a conflicting nucleotide sequence in a target sequence;
   (b) inserting a masking sequence into the conflicting sequence to produce a disrupted target sequence, wherein:
      (i) the masking sequence comprises recognition sites for one or more Type IIS restriction endonucleases; and
      (ii) digestion of said disrupted target sequence by said one or more Type IIS restriction endonucleases followed by re-ligation reconstitutes the target sequence;
   (c) synthesizing a polynucleotide comprising the disrupted target sequence using polymerase chain assembly; and
   (d) removing the masking sequence from said polynucleotide by digesting said polynucleotide with said one or more Type IIS restriction endonucleases followed by re-ligation of the digestion product, thereby producing a polynucleotide comprising said target sequence.

2. The method of claim 1, wherein said conflicting nucleotide sequence is a recognition sequence for an enzyme.

3. The method of claim 2, wherein said enzyme is a restriction enzyme.

4. The method of claim 1, wherein said conflicting sequence interferes with hybridization during said polymerase chain assembly.

5. The method of claim 4, wherein said conflicting sequence is a repeat sequence, an AT-rich region of low sequence diversity, a GC-rich region of low sequence diversity, or a homopolymeric tract.

6. The method of claim 1, wherein said target sequence is protein coding sequence.

7. The method of claim 1, wherein said target sequence encodes a regulatory RNA.

8. The method of claim 1, further comprising enzymatically processing said polynucleotide between steps (c) and (d).

9. The method of claim 8, wherein said enzymatically processing comprises circularizing said polynucleotide to produce a circular product.

10. The method of claim 9, wherein said enzymatically processing further comprise removing sequences from said polynucleotide by digesting said circular product with one or more restriction enzymes, followed by re-ligation, wherein said restriction enzymes do not digest the masking sequences.

11. The method of claim 1, wherein said removing the masking sequences is done on a polynucleotide that is in linear form.

12. The method of claim 1, wherein said one or more Type IIS restriction endonucleases are selected from BsaI, BsmB1, BbsI, SfaNI and HgaI.

13. The method of claim 1, wherein said masking sequence comprises two sites for a single Type IIS restriction endonuclease.

14. The method of claim 1, wherein said masking sequence is of 12-50 nucleotides in length.

15. The method of claim 1, further comprising: (e) cloning said target sequence into a vector.

16. The method of claim 1, wherein said vector is an expression vector designed for expression of said target sequence.

17. The method of claim 16, further comprising transferring said expression vector into a cell to produce an expression product encoded by said target sequence.

18. The method of claim 17, further comprising testing said expression product for an activity.

19. The method of claim 1, wherein the masking sequence is in the overlapping region of two overlapping oligonucleotides used in said polymerase chain assembly.

* * * * *